US00PP12873P2

(12) United States Plant Patent
VandenBerg

(10) Patent No.: US PP12,873 P2
(45) Date of Patent: Aug. 20, 2002

(54) CHRYSANTHEMUM PLANT NAMED 'WISH'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/757,504

(22) Filed: Jan. 11, 2001

(51) Int. Cl.[7] ..... A01H 5/00

(52) U.S. Cl. ..... Plt./287

(58) Field of Search ..... Plt./287, 291, 292

*Primary Examiner*—Howard J. Locker
(74) *Attorney, Agent, or Firm*—C. A. Whealy

(57) ABSTRACT

A distinct cultivar of Chrysanthemum plant named 'Wish', characterized by its large decorative-type inflorescences that are about 7.1 cm in diameter; attractive dark pink-colored ray florets; early flowering, response time about 54 days; dark green foliage; strong stems; and good postproduction longevity with inflorescences maintaining good substance and color for about three weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Wish'.

The new Chrysanthemum is a product of a planned breeding program conducted by the Inventor in Salinas, Calif. The objective of the breeding program is to create new cut Chrysanthemum cultivars having inflorescences with desirable colors and good form and substance.

The new Chrysanthemum originated from a cross made by the Inventor in January, 1994, in Salinas, Calif., of the Chrysanthemum cultivar Augusta, not patented, as the female, or seed, parent with a proprietary Chrysanthemum seedling selection identified as 1297, not patented, as the male, or pollen, parent.

The cultivar Wish was discovered and selected by the Inventor as a flowering plant within the progeny of the stated cross in a controlled environment in Salinas, Calif., in November, 1996. The selection of this plant was based on its desirable inflorescence colors and good form and substance.

Asexual reproduction of the new Chrysanthemum by terminal cuttings taken in a controlled environment in Salinas, Calif., has shown that the unique features of this new Chrysanthemum are stable and reproduced true to type in successive generations.

SUMMARY OF THE INVENTION

The cultivar Wish has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Wish'. These characteristics in combination distinguish 'Wish' as a new and distinct cultivar:

1. Large decorative-type inflorescences that are about 7.1 cm in diameter.
2. Attractive dark pink-colored ray florets.
3. Early flowering, response time about 54 days.

4. Dark green foliage.
5. Thick and strong stems.
6. Good postproduction longevity with inflorescences maintaining good substance and color for about three weeks in an interior environment.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Wish' grown as a spray-type cut Chrysanthemum.

The photograph on the second sheet comprises a close-up view of typical inflorescences of 'Wish'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on Feb. 10, 2000 and received 18 long day/short nights followed by short day/long nights until flowering. Plants were grown as single-stem spray-type cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Apr. 24, 2000.

Botanical classification: *Chrysanthemum×morifolium* cultivar Wish.

Commercial classification: Decorative-type cut Chrysanthemum.

Parentage:

*Female or seed parent.*—*Chrysanthemum×morifolium* cultivar Augusta, not patented.

*Male or pollen parent.*—Proprietary *Chrysanthemum×morifolium* seedling selection identified as code number 1297, not patented.

Propagation:

*Type.*—Terminal tip cuttings.

*Time to rooting.*—Seven to ten days with soil temperatures of 21° C.

*Root description.*—Fine, fibrous and well-branched.

Plant description:

*Appearance.*—Herbaceous decorative-type cut flower.

*Flowering stem description.*—Aspect: Erect. Length: About 96.5 cm. Spray width: About 21 cm. Diameter: About 7.5 mm. Internode length: About 3.4 cm. Texture: Pubescent. Color: Close to 144A.

*Foliage description.*—Arrangement: Alternate. Length: About 11.7 cm. Width: About 8 cm. Apex: Mostly mucronate. Base: Mostly truncate. Margin: Palmately lobed; sinuses mostly divergent. Texture: Upper and lower surfaces pubescent; leathery; veins prominent on lower surface. Color: Young foliage upper surface: Darker than 147A. Young foliage lower surface: Darker than 147B. Mature foliage upper surface: 147A; venation, close to 147B. Mature foliage lower surface: 147B; venation, close to 147B. Petiole: Length: About 1.9 cm. Diameter: About 3.5 mm. Color: Close to 147B to 147C.

Flowering description:

*Appearance.*—Decorative-type inflorescence form with elongated oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to about two to three weeks of long day/short night conditions after planting followed by photoinductive short day/long night conditions flower about 54 days later.

*Postproduction longevity.*—In an interior environment, flowering stems will maintain good color and substance for about three weeks in an interior environment after one week of cool storage.

*Quantity of inflorescences.*—Freely flowering with about 12 inflorescences per flowering stem.

*Inflorescence size.*—Diameter: About 7.1 cm. Depth (height): About 2.1 cm. Diameter of disc: About 5 mm, inconspicuous. Diameter of receptacle: About 9 mm.

*Ray florets.*—Shape: Elongated oblong, fused at base. Length: About 3.6 cm. Width: About 1.1 cm. Corolla tube length: About 5 mm. Corolla tube width, at base: About 1.5 mm. Apex: Acute or emarginate. Base: Fused. Texture: Satiny, smooth, glabrous. Aspect: Initially upright; when mature, about 90° from vertical; concave. Number of ray florets per inflorescence: About 249 arranged in numerous rows. Color: When opening, upper surface: 75A. When opening, lower surface: 75A to 75B. Mature, upper surface: 75A to 75B; fading to 75C to 75D with subsequent development. Mature, lower surface: 75A to 75C.

*Disc florets.*—Shape: Tubular; slightly flared at apex. Length: About 6 mm. Width: Apex: About 1.5 mm. Base: About 1 mm. Number of disc florets per inflorescence: Massed at center of receptacle, less than 15. Color: Immature: 144A. Mature: Apex: 9A. Mid-section and base: 155D.

*Peduncle.*—Aspect: Strong, angled about 45° from vertical. Length: First peduncle: About 9.3 cm. Fourth peduncle: About 13.2 cm. Seventh peduncle: About 16.7 cm. Diameter: About 2.5 mm. Texture: Very fine pubescence. Color: 144A.

*Reproductive organs.*—Androecium: Present on disc florets only. Anther color: 9A. Amount of pollen: Scarce. Pollen color: Close to 13A. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures lower than 40° C.

It is claimed:

1. A new and distinct cultivar of Chrysanthemum plant named 'Wish', as illustrated and described.

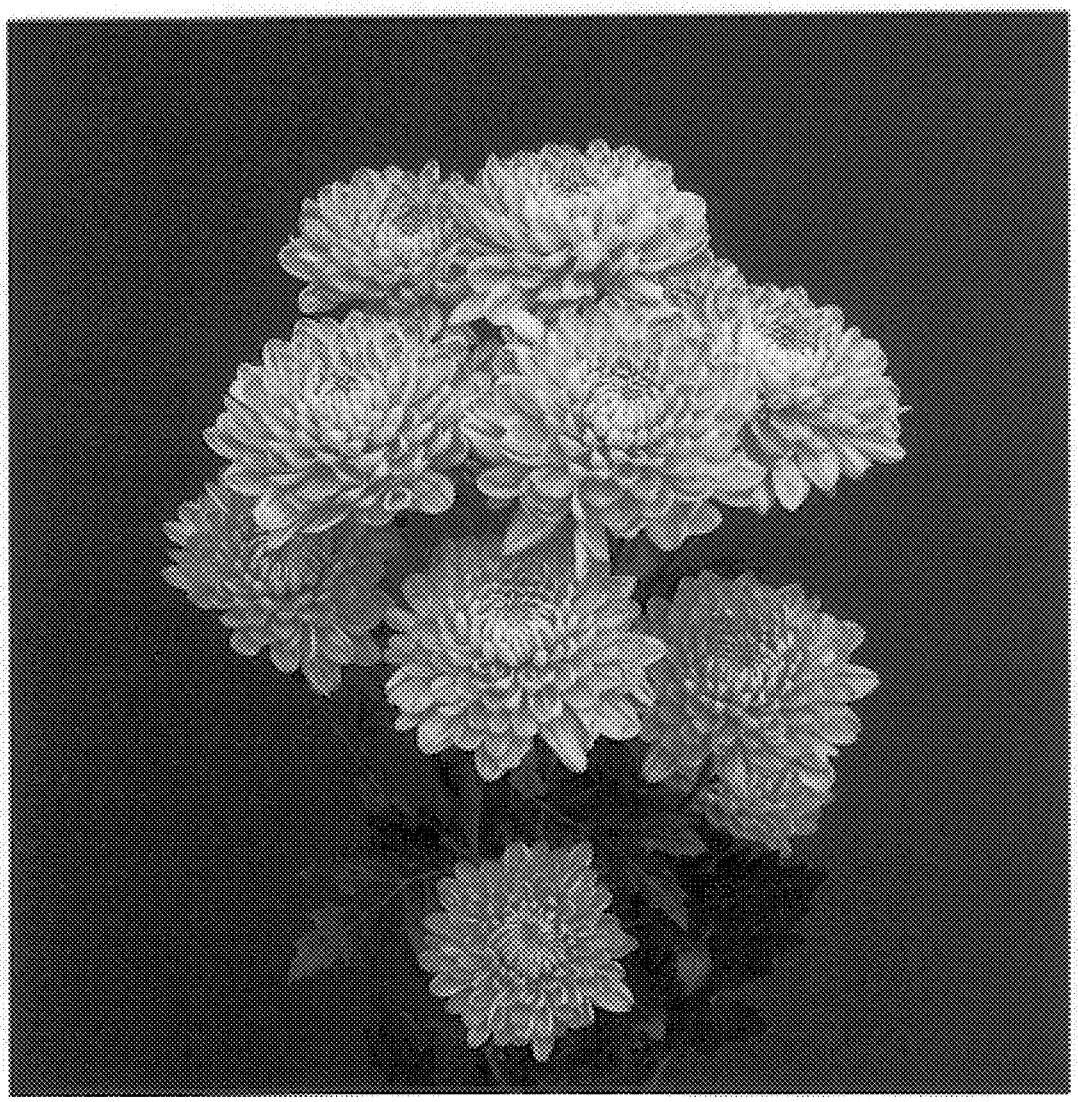

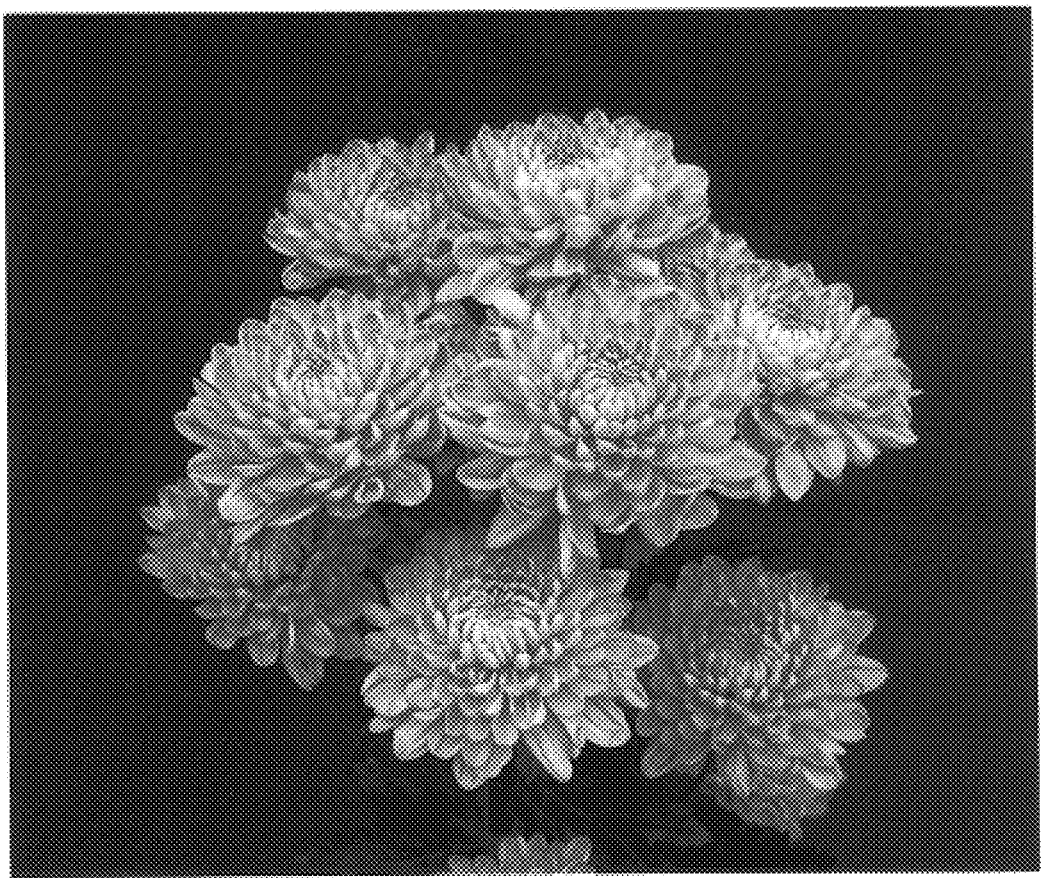

* * * * *